United States Patent [19]

Grundy

[11] Patent Number: 5,227,312
[45] Date of Patent: Jul. 13, 1993

[54] MONITORING PARTICLE AGGREGATION BY THE USE OF A MENISCUS

[75] Inventor: Martin A. Grundy, Dyfed, United Kingdom

[73] Assignee: Public Health Laboratory Service Board, London, England

[21] Appl. No.: 670,817

[22] Filed: Mar. 18, 1991

[51] Int. Cl.$^5$ ............... G01N 33/567; G01N 33/558; G01N 33/554; G01N 33/536; G01N 33/537; G01N 33/539; G01N 33.53; G01N 33/557; C12Q 1/00; C12M 1/24; C12M 1/06

[52] U.S. Cl. ..................... 436/517; 436/503; 436/514; 436/519; 436/536; 436/538; 436/539; 436/501; 435/7.1; 435/7.2; 435/7.25; 435/296; 435/315

[58] Field of Search .......... 435/7.1, 7.2, 7.25, 435/296, 315; 436/519, 520, 531, 524, 517, 501, 503, 514, 536, 538, 539

[56] References Cited

FOREIGN PATENT DOCUMENTS 2233089  2/1991  United Kingdom .

OTHER PUBLICATIONS

Grundy et al. (1989) J. Clin Lab Immunol 30:93–96.

*Primary Examiner*—Christine M. Nucker
*Assistant Examiner*—David R. Preston
*Attorney, Agent, or Firm*—Browdy and Neimark

[57] ABSTRACT

A method of monitoring the aggregation of cells in, for example, an immuno-agglutination assay, comprises promoting agglutination sonically in a capillary and inverting the capillary to cause agglutinated particles to settle at a meniscus. The granular appearance of agglutinated cells can be distinguished visually from the smooth distribution of non-aggregated cells.

11 Claims, 1 Drawing Sheet

MONITORING PARTICLE AGGREGATION BY THE USE OF A MENISCUS

BACKGROUND OF THE INVENTION

This invention relates to the aggregation of particles and in the most important example to the agglutination of biological cells through immuno-agglutination or otherwise.

It is well known that agglutination of cells in the presence of an antigen can form a useful assay technique. A commonly used screening test for Hepatitis B Virus (HBV) involves viral agglutination of specified erythrocytes coated with an antibody to the Hepatitis B surface antigen. The presence of antigen is confirmed by agglutination within 60 minutes, with agglutination being typically detected from the visual appearance of samples in a microwell plate.

There is a particular need for an HBV screening test that can be conducted very rapidly. In hospitals, for example, the time taken to complete an HBV screening on a newly admitted patient using presently known methods can significantly delay emergency surgery.

It is accordingly one object of this invention to provide a method of monitoring aggregation which can be used in haemagglutination or other tests to shorten the time taken to obtain a reliable result.

SUMMARY OF THE INVENTION

In one form, the present invention consists in a method of monitoring the aggregation of particles suspended in a liquid, comprising forming a meniscus at a surface of the liquid; causing the particles to settle at the meniscus and determining the distribution of settled particles over the meniscus.

In an important form of the invention, the particles are cells and the reaction-induced aggregation comprises immuno-agglutination.

It is found that the step of exposing the sample liquid to ultrasound considerably reduces the time required for haemagglutination or other reaction induced aggregation to take place. By causing the erythrocytes or other particles to settle on a meniscus, the presence of haemagglutination can be distinguished from mere sonic aggregation, the distribution of particles over the meniscus being distinguishable in the two cases, visually or otherwise.

The particles will often be cells but may take other forms. Plastics beads, for example, may have suitable surface binding sites promoting aggregation under defined conditions.

DETAILED DESCRIPTION OF PREFERRED EMBODIMENT

Figure 1:
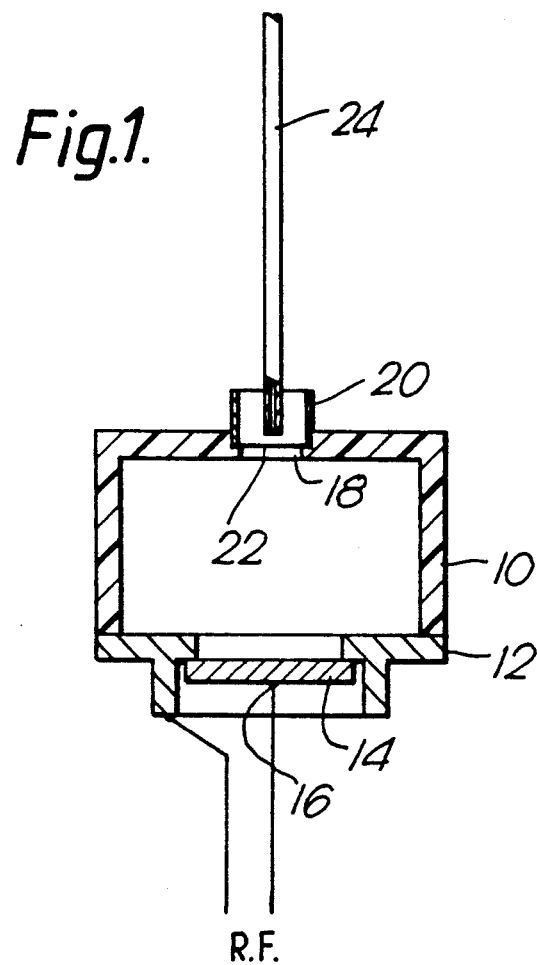
FIG. 1 is a diagrammatic section through apparatus for use in the present invention.

Referring to FIG. 1, a plastics housing 10 has an annular steel base ring 12 providing a mounting for a piezoelectric transducer 14. The transducer 14 comprises a disc of PZT having electrodes (not shown) provided on the opposing circular faces and being poled as a thickness expander having a resonance at 1 MHz. Connections via the base ring 12 and a terminal 16 on the lower surface of the transducer are taken to an rf amplifier which is not shown in the drawing.

An aperture 18 is provided in the housing 10 to receive a dish 20. This has relatively rigid side walls but a flexible base formed of 12 $\mu$m plastics film 22. The housing 10 is filled with a liquid such as water to provide a coupling between the transducer 14 and the dish 20.

Test cells in the form of lyophilised tanned turkey erythrocytes coated with purified horse antibody to the Hepatitis B surface antigen were prepared form a commercially available HBV screening test (Wellcome Diagnostics Limited: "Hepatitis B surface antigen HA Screening Kit"). Turkey erythrocytes coated with normal horse globulin were used as control cells. A positive control serum was prepared from heat inactivated diluted human serum containing HB surface antigen (obtained from Wellcome Diagnostics Limited) by 1:8 dilution in sterile phosphate buffered saline of pH 7.2 containing normal turkey serum, normal horse serum, normal human serum and sodium azide. A 1:8 dilution of normal human serum in a similar buffer served as a negative control serum.

Four types of sample were prepared as follows:
 i) Test cells plus positive serum.
 ii) Test cells plus negative serum.
 iii) Control cells plus positive serum.
 iv) Control cells plus negative serum.

Each sample was pipetted into the dish 20 in 250 $\mu$l volumes and thoroughly mixed. A glass capillary tube 24 of 2 mm internal diameter was lowered into the reaction mixture and about 30 $\mu$l of the mixture taken up into the capillary. The top of the capillary 24 was plugged with a suitable moldable material.

The PZT transducer was driven at 3 MHz with an output signal of 30 v peak to peak for a period of time varying from 30 to 180 seconds. At the end of the ultrasound period, the capillary was taken out of the reaction chamber and inverted. The moldable plug served to prevent movement of the droplet held in the capillary and provided a convenient base in which the inverted capillary may be supported.

During the application of ultrasound, the suspended cells became concentrated in bands perpendicular to the length of the capillary, these bands being separated by distances equivalent to half the acoustic wavelength (i.e. 0.25 mm at 3 MHz). When the capillary was removed from the acoustic field and inverted, redispersion of the aggregated cells was observed in cases where the exposure to ultrasound was for periods of 60 seconds or less. In cases of longer exposure to ultrasound, however, aggregates of cells remained intact, falling as clumps onto the meniscus at the lower surface of the sample droplet. After standing for two minutes, the meniscus was observed visually under ×8 magnification and a clear difference observed between the test cell/positive serum sample and the other three sample writers. Referring to FIG. 2a, samples ii), iii) and iv) were observed to produce a smooth ring around the base of the meniscus as disaggregated cells settled under the force of gravity. By contrast, and with reference to FIG. 2b, sample i) (test cell/positive serum) was observed to produce a marked granular appearance with clumps of agglutinated cells being spread over the meniscus.

The total time required to identify a positive or negative haemagglutination reaction was 5 minutes using the method according to this invention. A comparative test using the same kit conventionally in microwells required 30 minutes for haemagglutination to be identified. This time saving can be of considerable clinical significance. This is particularly so where concern over the risk of infection leads to a patient's medical attention being deferred until the results of an HBV screening test are known.

The technique of causing the agglutinated cells to settle on a meniscus to produce an observable distinction between haemagglutinated cells and cells merely aggregated acoustically, ingeniously avoids the need to handle or transport the agglutinated cells in an attempt to confirm haemagglutination. The cell aggregations are extremely fragile and any handling—for example to transfer the cells onto a microscope slide—runs the substantial risk of breaking up the aggregation, whether or not haemagglutination has taken place.

Whilst visual observation of the distribution of cells is simple and convenient, it might be replaced in automated, multiple sample assays by appropriate optical detection means. As will appear to the skilled man, it is a relatively straightforward matter using known image analysis techniques to distinguish between the smooth ring associated with a negative result and the marked granular appearance which indicates a positive result.

It should be understood that inversion of a capillary is but one example of ways according to this invention in which cells or other particles can be caused to settle at a meniscus. The meniscus can be formed at the interface of two immiscible liquids, not necessarily at a liquid/gas boundary as in the described example. Whilst settling of the particles under gravity is both simple and effective, it will be appropriate in some cases to utilise electrostatic or other forces to move the particles towards the meniscus.

In addition to the monitoring of haemo-agglutination, the invention will find application in monitoring the aggregation of cells, coated plastic beads or still other particles, induced by proteins or otherwise polymers.

What is claim is:

1. A method of monitoring the aggregation of particles suspended in a liquid resulting from an agglutination process, comprising forming a meniscus of a surface of the liquid; causing the particles through gravity or otherwise to move towards and settle at the meniscus; and determining the distribution of settled particles over the meniscus.

2. A method according to claim 1, wherein agglutination is promoted by the exposure of said liquid to ultrasound, said distribution of settled particles distinguishing between agglutination and mere sonic aggregation.

3. A method according to claim 2, wherein said agglutination process comprises immuno-agglutination.

4. A method according to claim 1, wherein said meniscus is formed at a liquid/air boundary.

5. A method according to claim 1, wherein the step of causing particles to settle on the meniscus includes inverting a vessel containing said liquid.

6. A method according to claim 1, wherein said particles comprise cells.

7. A method according to claim 1, wherein said liquid is within a capillary; and wherein said causing of the particles to settle at the meniscus is effected by applying ultrasound to said liquid with a transducer means and using an acoustic coupling means serving to couple the liquid in the capillary with the transducer means, followed by inversion of said capillary.

8. Apparatus for monitoring the aggregation of particles suspended in a liquid resulting from an agglutination process, comprising a capillary containing said liquid; ultrasound transducer means; acoustic coupling means serving to couple the liquid in said capillary with the transducer means, the capillary being capable of inversion to cause particles through gravity to move towards and settle at a meniscus formed in said capillary.

9. Apparatus according to claim 8, wherein said acoustic coupling means comprises a body of liquid.

10. An immuno-agglutination assay comprising the steps of applying ultrasound energy to a liquid suspension of prepared test cells containing sample serum; forming a meniscus at a surface of the liquid; causing agglutinated cells through gravity or otherwise to settle at said meniscus; and examining said cells to determine the distribution thereof over said meniscus.

11. An assay according to claim 10, comprising the step of inverting a vessel containing said liquid to cause the agglutinated cells to settle at the meniscus.

* * * * *